(12) United States Patent
Sternberg et al.

(10) Patent No.: US 10,996,205 B2
(45) Date of Patent: May 4, 2021

(54) STRESS BIOMARKERS AND RELATED NON-INVASIVE DETECTION METHODS

(71) Applicant: ARIZONA BOARD OF REGENTS ON BEHALF OF THE UNIVERSITY OF ARIZONA, Tucson, AZ (US)

(72) Inventors: Esther M. Sternberg, Tucson, AZ (US); Min Jia, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 273 days.

(21) Appl. No.: 15/777,536

(22) PCT Filed: Nov. 18, 2016

(86) PCT No.: PCT/US2016/062860
§ 371 (c)(1),
(2) Date: May 18, 2018

(87) PCT Pub. No.: WO2017/087852
PCT Pub. Date: May 26, 2017

(65) Prior Publication Data
US 2018/0348176 A1   Dec. 6, 2018

Related U.S. Application Data

(60) Provisional application No. 62/257,558, filed on Nov. 19, 2015.

(51) Int. Cl.
| | | |
|---|---|---|
| G01N 30/72 | (2006.01) | |
| G01N 33/50 | (2006.01) | |
| G01N 33/74 | (2006.01) | |
| G01N 1/40 | (2006.01) | |
| G01N 30/88 | (2006.01) | |

(52) U.S. Cl.
CPC ..... *G01N 30/7233* (2013.01); *G01N 33/5088* (2013.01); *G01N 33/743* (2013.01); *G01N 30/72* (2013.01); *G01N 2001/4061* (2013.01); *G01N 2030/8813* (2013.01); *G01N 2333/575* (2013.01); *G01N 2800/7004* (2013.01)

(58) Field of Classification Search
CPC .............. G01N 30/7233; G01N 30/72; G01N 33/5088; G01N 33/743; G01N 2001/4061; G01N 2333/575; G01N 2030/88113; G01N 2800/7004
See application file for complete search history.

(56) References Cited

U.S. PATENT DOCUMENTS

| | | |
|---|---|---|
| 5,676,144 A | 10/1997 | Schoendorfer |
| 5,730,986 A | 3/1998 | Bandyopadhyay et al. |
| 2004/0137420 A1 | 7/2004 | Yasuda et al. |
| 2007/0055456 A1 | 3/2007 | Raftery et al. |
| 2011/0003395 A1* | 1/2011 | Dey ........................ G01N 33/64 436/98 |
| 2013/0252319 A1* | 9/2013 | Jung ................... G01N 27/3276 435/287.2 |

FOREIGN PATENT DOCUMENTS

| | | |
|---|---|---|
| CN | 104897835 | 9/2015 |
| RU | 2008 127 779 | 1/2010 |

OTHER PUBLICATIONS

Lenze, Eric J. et al. "Elevated cortisol in older adults with Generalized Anxiety Disorder is reduced by treatment: a placebo-controlled evaluation of escitaloprann." Am J. Geriatr Psych (2011) 19 482.490. (Year: 2011).*
Meno-Bravo, A. et al. "Sweat: a sample with limited present applications and promising future in metabolomics." J. Pharm. Biomed. Analysis (2014) 90 139-147. (Year: 2014).*
Toshiaski, Usui et al. "A simplified method for the estimation of urinary free cortisol and 20-dihydrocortisol by fluorometry." Clinica Chinnica Acta (1970) 30 595-601. (Year: 1970).*
International Search Report and Written Opinion, International Patent Application No. PCT/US2016/062860, dated Feb. 2, 2017, 14 pages.
Russell, E. et al. The detection of cortisol in human sweat: implications for measurement of cortisol in hair. Ther Drug Monit. Feb. 2014;36(1):30-4.
Hill, EE et al. Exercise and circulating cortisol levels: the intensity threshold effect, J Endocrinol Invest. Jul. 2008;31(7):587-91.
Marques-Deak, A. et al. Measurement of cytokines in sweat patches and plasma in healthy women: validation in a controlled study, J. Immunol. Methods, 2006, 315:99-109.
Jia, M. et al., Development of a Sensitive Microarray Immunoassay for the Quantitative Analysis of Neuropeptide Y, Anal Chem. Aug. 2012:7;84(15):6508-14.
Cizza, G. et al. Elevated neuroimmune biomarkers in sweat patches and plasma of premenopausal women with major depressive disorder in remission: the POWER study, Biol Psychiatry. Nov. 15, 2008;64(10):907-11.
Dodds, H.M. et al., A High-Performance Liquid Chromatography—Electrospray—Tandem Mass Spectrometry Analysis of Cortisol and Metabolites in Placental Perfusate, Analytical Biochemistry, 247, 342-347(1997).
Bocchi, B. et al. Impaired 11-β Hydroxysteroid Dehydrogenase Type 2 Activity in Sweat Gland Ducts in Human Essential Hypertension, Hypertension, 2004, 43(4), 803-808.

\* cited by examiner

*Primary Examiner* — Christopher Adam Hixson
(74) *Attorney, Agent, or Firm* — Casimir Jones, S.C.; Robert A. Goetz

(57) ABSTRACT

Provided herein are kits, compositions and methods for biomarker detection, and the use of relative or absolute levels of these markers for non-invasive detection of stress and/or relaxation levels in human subjects. In particular, the present invention relates to cortisol, isomer and metabolite markers for stress and/or relaxation levels.

5 Claims, 8 Drawing Sheets

STRESS BIOMARKERS AND RELATED NON-INVASIVE DETECTION METHODS

CROSS-REFERENCE TO RELATED APPLICATIONS

This application is a U.S. 371 national phase entry of International Patent Application No. PCT/US2016/062860, filed Nov. 18, 2016, which claims priority to and the benefit of U.S. Provisional Application No. 62/257,558, filed Nov. 19, 2015, the contents of which are hereby incorporated by reference in their entireties.

FIELD OF THE INVENTION

Provided herein are kits, compositions and methods for biomarker detection, and the use of relative or absolute levels of these markers for non-invasive detection of stress and/or relaxation levels in human subjects. In particular, the present invention relates to cortisol, isomer and metabolite markers for stress and/or relaxation levels.

BACKGROUND OF THE INVENTION

Cortisol, the adrenal glands' principle stress hormone, is a small steroid hormone (MW: 362.46) that plays many important roles in physiological and psychological processes. It is secreted by the adrenal glands, as an end product of the hypothalamic-pituitary-adrenal (HPA) axis mainly in response to stress. Cortisol is crucial for homeostatic maintenance, by means of modulating, regulating or influencing vital systems including neural, immune, cardiovascular, metabolic, and endocrine systems. Abnormal circulating cortisol levels lead to illness. Prolonged elevated levels can cause impaired cognitive performance, hyperglycemia, sleep disruption, elevated blood pressure, suppressed immune function, obesity, fatigue; and are reported to contribute to the development of Cushing's disease. Chronically lower levels (adrenal fatigue) have been associated with fatigue, low blood pressure and inflammation.

A variety of analytical techniques have been employed for cortisol analysis in biofluids, including radio immunoassay (RIA), enzyme-linked immunosorbent assay (ELISA), chemiluminescence immunoassay (CLIA), capillary electrophoresis-based immunoassay (CE-IA), miniaturized immunosensors, gas chromatography-mass spectrometry (GC-MS) and high performance liquid chromatography-tandem mass spectrometry (HPLC-MS/MS). Although still widely adopted in biomedical and clinical studies, immunoassays of cortisol are known to suffer from specificity problems due to antibody cross-reaction with other unidentified endogenous steroids, administered drugs as well as their markers, which lead to false positive results that could invalidate clinical test results.

Cortisol has been routinely measured in human blood, urine and saliva in clinical labs. It has also been detected in interstitial fluid (ISF) and hair. Among these, blood and ISF samplings are invasive, which can alter the stress level of patients, and thereby introduce artifacts and erroneous results. Although collection of urine and saliva are non-invasive, these have potential reliability problems as a source biofluid for cortisol detection.

Based on the above background, a simple, sensitive, and specific analytical method for accurate quantification of cortisol, isomer and metabolite markers in human eccrine sweat is needed to non-invasively measure this important stress hormone in settings where collection of blood is unfeasible or undesirable.

SUMMARY OF THE INVENTION

During experiments conducted in the course of developing embodiments for the present invention, a sensitive HPLC-tandem mass spectrometry method was developed for the quantitation of cortisol ((11$\beta$)-11,17,21-Trihydroxy-pregn-4-ene-3,20-dione) and related metabolites in human eccrine sweat. These markers were prepared from human eccrine sweat by liquid-liquid extraction using ethyl acetate. At least one unknown cortisol isomer that has previously not been reported and could potentially interfere with quantification was separated from cortisol with reversed phase HPLC. Detection of cortisol and metabolites was carried out using atmospheric pressure chemical ionization (APCI) and selected reaction monitoring (SRM) in positive ion mode, using cortisol-9,11,12,12-D4 as internal standard. LOD and LOQ for cortisol were estimated to be 0.04 ng/ml and 0.1 ng/ml, respectively. Linear range of 0.10-25.00 ng/ml was obtained. Intraday precision (2.5%-9.7%) and accuracy (0.5%-2.1%), interday precision (12.3%-18.7%) and accuracy (7.1%-15.1%) were achieved. This method has been successfully applied to the cortisol analysis of human eccrine sweat samples. This is the first demonstration that HPLC-tandem mass spectrometry can be used for the sensitive and highly specific determination of cortisol in human eccrine sweat in the presence of at least one isomer that has very similar hydrophobicity as cortisol. Such experiments demonstrated that human eccrine sweat can be used as a source for non-invasive assessment of stress biomarkers such as cortisol and other steroid hormones.

Accordingly, provided herein are kits, compositions and methods for biomarker detection, and the use of relative or absolute levels of these markers for non-invasive detection of stress levels in human subjects. In particular, the present invention relates to cortisol, isomer and metabolite markers for stress levels.

In some embodiments, the present invention provides methods of detecting one or more of cortisol, cortisone, 20$\alpha$-dihydrocortisone, 20$\beta$-dihydrocortisone, 20$\alpha$-dihydrocortisol, and 20$\beta$-dihydrocortisol in a sweat sample from a subject. Such methods are not limited to a particular manner of detecting the one or more of cortisol, cortisone, 20$\alpha$-dihydrocortisone, 20$\beta$-dihydrocortisone, 20$\alpha$-dihydrocortisol, and 20$\beta$-dihydrocortisol. In some embodiments, such methods comprise, for example, analyzing a human sweat sample from a subject with chromatograpy-mass spectrometry assay to determine the presence, absence, or levels of the one or more of cortisol, cortisone, 20$\alpha$-dihydrocortisone, 20$\beta$-dihydrocortisone, 20$\alpha$-dihydrocortisol, and 20$\beta$-dihydrocortisol in the sample. In some embodiments, the methods include determining the presence, absence, or levels of each of cortisol, cortisone, 20$\alpha$-dihydrocortisone, 2013-dihydrocortisone, 20$\alpha$-dihydrocortisol, and 20$\beta$-dihydrocortisol.

Such methods are not limited to a particular type of sample. In some embodiments, the sample is an eccrine sweat sample.

Such methods are not limited to a particular type of subject. In some embodiments, the subject is a mammalian subject. In some embodiments, the subject is a human subject.

Such methods are not limited to a particular type of chromatography. In some embodiments, the chromatography is UHPLC (e.g., reverse phase UHPLC).

Such methods are not limited to a particular type of mass spectrometry. In some embodiments, the mass spectrometry is, for example, Q-TOF MS, QqQ, or LTQ Orbitrap. In some embodiments, the MS is MS-MS.

In some embodiments, the sample is extracted with ethyl acetate prior to the analysis.

In some embodiments, an increased or decreased level (e.g., relative or absolute level) of the one or more of cortisol, cortisone, 20α-dihydrocortisone, 20β-dihydrocortisone, 20α-dihydrocortisol, and 20β-dihydrocortisol is correlated with stress levels in the subject. For example, in some embodiments, increasing amounts of such markers over a time period indicates an increasing amount of stress in the subject. For example, in some embodiments, decreasing amounts of such markers over a time period indicates an decreasing amount of stress in the subject. For example, in some embodiments, little or no change in the amounts of such markers over a time period indicates an unchanged amount of stress in the subject. For example, in some embodiments, changes in levels of these biomarkers (e.g., increases or decreases) inversely correlates with increased or decreased stress levels.

In some embodiments, the level (e.g., relative or absolute level) of the one or more of cortisol, cortisone, 20α-dihydrocortisone, 20β-dihydrocortisone, 20α-dihydrocortisol, and 2013-dihydrocortisol is correlated with stress in the subject. For example, in some embodiments, the level of the one or more of cortisol, cortisone, 20α-dihydrocortisone, 20β-dihydrocortisone, 20α-dihydrocortisol, and 20β-dihydrocortisol is compared with known reference levels of such markers associated with certain stress levels (e.g., reference levels of such markers associated with no stress) (e.g., reference levels of such markers associated with low levels of stress) (e.g., reference levels of such markers associated with moderate levels of stress) (e.g., reference levels of such markers associated with high levels of stress) (e.g., reference levels of such markers associated with very high levels of stress) (e.g., reference levels of such markers associated with toxic levels of stress (e.g., levels of stress high enough to induce physical and/or mental damage to the subject)).

Such methods are not limited to generating the known reference levels for types of stress. In some embodiments, the known reference levels are generated from groups of subjects (e.g., 5, 10, 50, 100, 1000, 10000, etc) experiencing the specific type of stress. In some embodiments, the groups of subjects are specific to a particular age (e.g., 0-1 years of age, 2-4 years of age, 5-8 years of age, 9-12 years of age, 13-15 years of age, 16-18 years of age, 19-25 years of age, 26-35 years of age, 35-50 years of age, 50-60 years of age, over 60 years of age) (e.g., any specific age or age range). In some embodiments, the groups of subjects are specific for gender. In some embodiments, the groups of subjects is a mix of gender. In some embodiments, the groups of subjects are specific to a particular psychiatric profile (e.g., no history of mental illness; history of mental illness; no recent history of mental illness; currently experiencing mental illness). In some embodiments, the groups of subjects are specific for subjects experiencing an anxiety disorder, major depressive disorder (MDD) or other forms of depression, post-traumatic stress disorder (PTSD), traumatic brain injury (TBI), a psychotic disorder, and/or a personality disorder. In some embodiments, the groups of subjects are specific for subjects experiencing any disorder recognized in a relevant field medicine (e.g., psychiatry).

In some embodiments, such methods are used to characterize stress in persons with or those at risk for autoimmune/inflammatory or allergic disorders, or those with disorders who are relatively resistant to steroid treatment (e.g. steroid resistant asthma; systemic lupus erythematosus).

In some embodiments, such methods are used to characterize stress in pregnant women having or at risk for having conditions where fetal health may be compromised by excessive stress levels, and the fetal risk for stress-related conditions.

In some embodiments, such methods are used to characterize stress in subjects experiencing aging and/or frailty of aging, and their risk for developing frailty.

In some embodiments, such methods are used to characterize stress responses in subjects experiencing skin aging and/or frailty of skin aging, and their risk for developing these conditions.

In some embodiments, such methods are used to characterize stress in subjects having stress-related disorders, and their risk for developing these conditions, including but not limited to diabetes, obesity, prolonged wound healing, certain cancers, increased susceptibility to and severity of infectious diseases (viral, bacterial), and poor vaccine/immunization take-rate.

In some embodiments, such methods are used to characterize stress in and/or diagnose subjects with endocrine disorders, including but not limited to Cushings disease.

In some embodiments, such methods are used to characterize stress in subjects with stress-related burn-out, and their risk for developing this condition.

In some embodiments, such methods are used for developing pharmaceutical agents targeted at decreasing stress in subjects (e.g., through targeting one or more of cortisol, cortisone, 20α-dihydrocortisone, 20β-dihydrocortisone, 20α-dihydrocortisol, and 20β-dihydrocortisol) (e.g., through decreasing the level of one or more of cortisol, cortisone, 20α-dihydrocortisone, 20β-dihydrocortisone, 20α-dihydrocortisol, and 20β-dihydrocortisol).

In some embodiments, such methods are used for developing pharmaceutical agents targeted at increasing stress and/or stress responses in subjects (e.g., through targeting one or more of cortisol, cortisone, 20α-dihydrocortisone, 20β-dihydrocortisone, 20α-dihydrocortisol, and 20β-dihydrocortisol) (e.g., through increasing the level of one or more of cortisol, cortisone, 20α-dihydrocortisone, 20β-dihydrocortisone, 20α-dihydrocortisol, and 20β-dihydrocortisol) (e.g., through targeting one or more cortisol metabolizing enzymes responsible for producing these biomarkers). In some embodiments, such methods are used for increasing cortisol levels in cortisol deficient conditions, to treat burn-out in which cortisol levels are low, and/or to abrogate cortisol/steroid treatment resistant conditions.

In some embodiments, the method further comprises the step of determining the presence of elevated stress levels in the subject when the levels (e.g., relative or absolute levels) of the one or more of cortisol, cortisone, 20α-dihydrocortisone, 20β-dihydrocortisone, 20α-dihydrocortisol, and 20β-dihydrocortisol are increased or decreased relative to the levels in a subject not experiencing stress.

In some embodiments, the method further comprises the step of reporting the presence of elevated stress to the subject and/or health professional.

Such methods are not limited to obtaining a sweat sample. In some embodiments, the human sweat sample is obtained through use of a skin contact patch or similar sample collection apparatus. In some cases, the one or more of cortisol, cortisone, 20α-dihydrocortisone, 20β-dihydrocortisone, 20α-dihydrocortisol, and 20β-dihydrocortisol are detected without actual collection of sweat.

In certain embodiments, the present invention provides methods of measuring stress and/or relaxation levels in a subject, comprising: a) analyzing a human sweat sample from a subject with chromatograpy-mass spectrometry assay to determine the presence, absence, or level of one or more of cortisol, cortisone, 20α-dihydrocortisone, 20β-dihydrocortisone, 20α-dihydrocortisol, and 20β-dihydrocortisol in the sample; and b) determining the presence of elevated stress levels in the subject when the levels (e.g., relative or absolute levels) of the one or more of cortisol, cortisone, 20α-dihydrocortisone, 20β-dihydrocortisone, 20α-dihydrocortisol, and 20β-dihydrocortisol are increased or decreased relative to the levels in a subject not experiencing stress. In some embodiments, an increased or decreased level of cortisol, cortisone, 20α-dihydrocortisone, 20β-dihydrocortisone, 20α-dihydrocortisol, and 20β-dihydrocortisol in the sample relative to the normal level of the subject is indicative of elevated stress levels in the subject. In some embodiments, the human sweat sample is obtained through use of a skin contact patch or similar sample collection apparatus (e.g., patch, device, empirical method).

Additional embodiments are described herein.

DEFINITIONS

Figure 1:
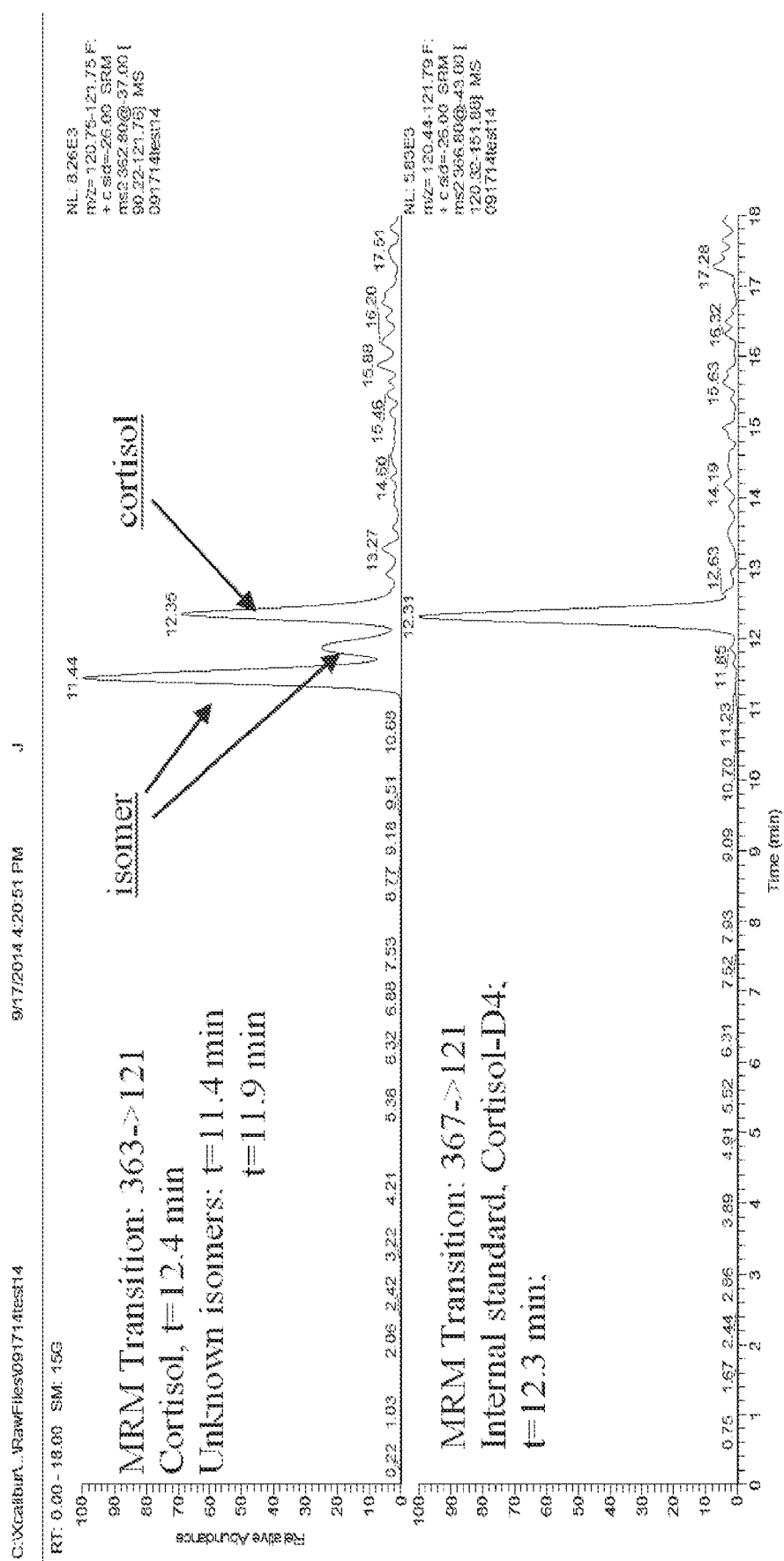
FIG. 1. Typical extracted ion chromatogram (EIC) of cortisol and its isomers in human eccrine sweat (MRM 363→121 transition, QQQ).
Figure 2:
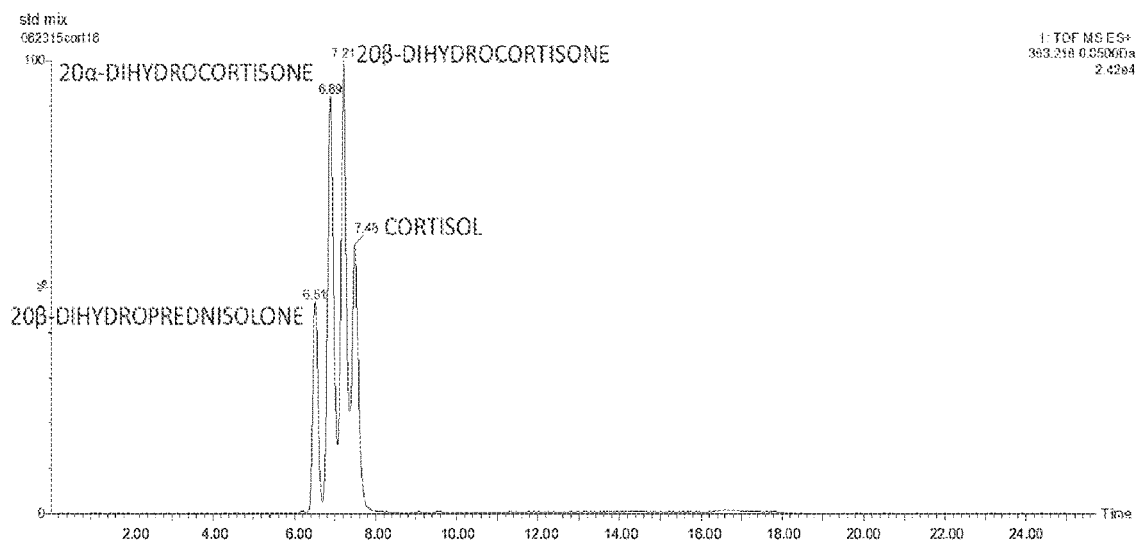
FIG. 2. Mass spectrometry chromatogram showing cortisol and 20α-dihydrocortisone and 20β-dihydrocortisone isomer standards (QTOF).

To facilitate an understanding of the present invention, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, the terms "detect", "detecting", or "detection" may describe either the general act of discovering or discerning or the specific observation of a detectably labeled composition.

The term "sample" in the present specification and claims is used in its broadest sense. On the one hand it is meant to include a specimen or culture. On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc. A biological sample may contain any biological material suitable for detecting the desired biomarkers, and may comprise cellular and/or non-cellular material from a subject. The sample can be isolated from any suitable biological tissue or fluid such as, for example, prostate tissue, blood, blood plasma, urine, or cerebral spinal fluid (CSF).

A "reference level" of a marker means a level of the marker that is indicative of a particular disease state, stress level, phenotype, or lack thereof, as well as combinations of disease states, phenotypes, or lack thereof. A "positive" reference level of a marker means a level that is indicative of a particular disease state or phenotype. A "negative" reference level of a marker means a level that is indicative of a lack of a particular disease state or phenotype. A "reference level" of a marker may be an absolute or relative amount or concentration of the marker, a presence or absence of the marker, a range of amount or concentration of the marker, a minimum and/or maximum amount or concentration of the marker, a mean amount or concentration of the marker, and/or a median amount or concentration of the marker. Appropriate positive and negative reference levels of marker for a particular disease state, phenotype, or lack thereof may be determined by measuring levels of desired marker in one or more appropriate subjects, and such reference levels may be tailored to specific populations of subjects (e.g., a reference level may be age-matched so that comparisons may be made between marker levels in samples from subjects of a certain age and reference levels for a particular disease state, phenotype, or lack thereof in a certain age group). Such reference levels may also be tailored to specific techniques that are used to measure levels of marker in biological samples (e.g., LC-MS, GC-MS, etc.), where the levels of marker may differ based on the specific technique that is used.

The term "separation" refers to separating a complex mixture into its component proteins or markers. Common laboratory separation techniques include gel electrophoresis and chromatography.

The term "chromatography" refers to a physical method of separation in which the components to be separated are distributed between two phases, one of which is stationary (stationary phase) while the other (the mobile phase) moves in a definite direction. Chromatographic output data may be used for manipulation by the present invention.

The term "retention time", when used in the context of mass spectrometry data, refers to the elapsed time in a chromatography process since the injection of the sample into the separation device. A "mass analyzer" is a device in a mass spectrometer that separates a mixture of ions by their mass-to-charge ratios.

A "source" is a device in a mass spectrometer that ionizes a sample to be analyzed.

A "detector" is a device in a mass spectrometer that detects ions.

An "ion" is a charged object formed by adding electrons to or removing electrons from an atom or molecule.

A "mass spectrum" is a plot of data produced by a mass spectrometer, typically containing m/z values on x-axis and intensity values on y-axis.

A "peak" is a point on a mass spectrum with a relatively high y-value.

The term "m/z" refers to the dimensionless quantity formed by dividing the mass number of an ion by its charge number. It has long been called the "mass-to-charge" ratio. As used herein, the terms "detect", "detecting", or "detection" may describe either the general act of discovering or discerning or the specific observation of a detectably labeled composition.

DETAILED DESCRIPTION OF THE INVENTION

Described herein is the development and validation of a sensitive and specific liquid chromatography—tandem mass spectrometry method for detection of cortisol and related markers in human eccrine sweat. In experiments described herein, baseline separation of cortisol from at least one unknown interfering isomer(s) and other metabolites was achieved. It was shown that with this method, as low as 0.04 ng/ml of cortisol could be detected in artificial sweat, with a linear range from 0.10 ng/ml to 25.00 ng/ml. Two sets of thermally induced sweat samples collected in a hot chamber at approximately 1 and 4 pm on the same day were analyzed and cortisol concentrations ranging from 2.80 to 0.24 ng/ml were obtained in these samples. Sweat cortisol levels were different at different times of the day, corresponding to the diurnal effects in plasma cortisol levels. It was determined that cortisone, 20α-dihydrocortisone, 20β-dihydrocortisone, 20α-dihydrocortisol, and 20β-dihydrocortisol have different relative abundance among individuals, and in particular, different relative abundance depending on the amount of stress experienced among a specific individual.

Accordingly, provided herein are methods of detecting cortisol, cortisone, 20α-dihydrocortisone, 20β-dihydrocortisone, 20α-dihydrocortisol, and 20β-dihydrocortisol in a sweat sample from a subject. In some embodiments, the levels of cortisol, cortisone, 20α-dihydrocortisone, and 20β-dihydrocortisone, 20α-dihydrocortisol, 20β-dihydrocortisol are compared with reference levels (e.g., the levels in a healthy subject, the levels in the same subject at different times, pre-determined reference levels, change in reference or test levels over time, etc.) to determine the presence of elevated stress levels in the subject. In some embodiments, an increased or decreased level (e.g., relative or absolute level) of cortisol, cortisone, 20α-dihydrocortisone, 20β-dihydrocortisone, 20α-dihydrocortisol, and 20β-dihydrocortisol relative to the reference level is indicative of the presence of an elevated stress level in the subject.

The sweat samples are obtained from subjects using any suitable method (e.g., those described in the experimental section). In some embodiments, sweat samples are processed (e.g., by ethyl acetate extraction) prior to analysis.

Markers (e.g, cortisol, cortisone, 20α-dihydrocortisone, 20β-dihydrocortisone, 20α-dihydrocortisol, and 20β-dihydrocortisol) may be detected using any suitable method including, but not limited to, liquid and gas phase chromatography, alone or coupled to mass spectrometry (See e.g., experimental section below), NMR (See e.g., US patent publication 20070055456, herein incorporated by reference), immunoassays, chemical assays, spectroscopy and the like. In some embodiments, commercial systems for chromatography, mass spectrometry, and NMR analysis are utilized.

In other embodiments, markers (e.g., biomarkers and derivatives thereof) are detected using optical imaging techniques such as magnetic resonance spectroscopy (MRS), magnetic resonance imaging (MRI), CAT scans, ultra sound, MS-based tissue imaging or X-ray detection methods (e.g., energy dispersive x-ray fluorescence detection). In other embodiments, electrochemical, field effect conductor, and/or optical methods (e.g., fluorescence) are used as sensors (e.g., wearable sensors) (e.g., a wearable sensor format for real time marker measurement).

Any suitable method may be used to analyze the biological sample in order to determine the presence, absence or level(s) of the one or more markers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, biochemical or enzymatic reactions or assays, and combinations thereof. Further, the level(s) of the one or more markers may be measured indirectly, for example, by using an assay that measures the level of a compound (or compounds) that correlates with the level of the biomarker(s) that are desired to be measured. In some embodiments, the mass spectrometry is, for example, Q-TOF MS, QqQ, or LTQ Orbitrap.

In some embodiments, a computer-based analysis program is used to translate the raw data generated by the detection assay (e.g., the presence, absence, or amount of a marker) into data of predictive value for a clinician. The clinician can access the predictive data using any suitable means. Thus, in some embodiments, the present invention provides the further benefit that the clinician, who is not likely to be trained in marker analysis, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a swesat sample) is obtained from a subject and submitted to a profiling service (e.g., clinical lab at a medical facility, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., metabolic profile), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of elevated stress being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may choose further intervention or counseling based on the results. In some embodiments, the data is used for research use. For example, the data may be used to further optimize the inclusion or elimination of markers as useful indicators of a particular condition or stage of disease.

Compositions for use (e.g., sufficient for, necessary for, or useful for) in the diagnostic methods of some embodiments of the present invention include reagents for detecting the presence or absence of markers described herein. Any of these compositions, alone or in combination with other compositions of the present invention, may be provided in the form of a kit. Kits may further comprise appropriate controls and/or detection reagents.

In some embodiments, the present invention provides drug screening assays (e.g., to screen for drugs that reduce or prevent stress).

EXPERIMENTAL

The following examples are provided in order to demonstrate and further illustrate certain preferred embodiments and aspects of the present invention and are not to be construed as limiting the scope thereof.

Example 1

Experimental Section
Materials
Cortisol (4-PREGNEN-11β, 17, 21-TRIOL-3, 20-DIONE), cortisone (4-PREGNEN-17, 21-DIOL-3, 11, 20-TRIONE), 20α-DIHYDROCORTISONE (4-PREGNEN-17, 20α, 21-TRIOL-3, 11-DIONE), 20β-DIHYDROCORTISONE (4-PREGNEN-17, 20β, 21-TRIOL-3, 11-DIONE), 20α-DIHYDROCORTISOL (4-PREGNEN-11β, 17, 20α, 21-TETROL-3-ONE), 20β-DIHYDROCORTISOL (4-PREGNEN-11β, 17, 20β, 21-TETROL-3-ONE)>98% was purchased from Steraloids, Inc (Newport, R.I.). HPLC grade acetonitrile was bought from Fisher Scientific (Fair Lawn, N.J.); HPLC grade water was bought from J. T. Baker, Inc. (Phillipsburg, N.J.); formic acid (98%) was purchased from EMD Chemicals Inc. (Gibbstown, N.J.). Artificial eccrine perspiration was bought from Pickering Laboratories, Inc. (Mountain View, Calif.); Cortisol-9,11,12,12-D4 (97% atom % D) was obtained from CDN Isotopes Inc. (Pointe-Claire, Quebec, Canada).
Working Standard Solution Preparation
Storage is at room temperature for cortisol (F), cortisone (E) and cortisol-D4 (F-D4) or −20° C. for 20 α-dihydrocortisone (20 α-DHE), 20 β-dihydrocortisone (20 β-DHE), 20 α-dihydrocortisol (20 α-DHF), 20 β-dihydrocortisol (20 β-DHF). Cortisol-D4 (internal standard) is prepared to 250 ng/ml in 10% acetonitrile and stored at −20° C. before use. Stock standards are prepared separately to a concentration of 2 mg/ml in methanol. Mixed working standards are prepared to the concentrations using 10% acetonitrile as the diluent. Working quality control standards were aliquoted and stored at −20° C. throughout the validation period.
Human Eccrine Sweat Collection and Preparation All eccrine sweat samples were handled in accordance with approved institutional review board (IRB) protocols at University of Arizona School of Medicine. Sweat was induced via exercise at room temperature on a stationary bike located at Arizona Clinical and Translational Sciences Research Center (CATS). Subjects had free access to water during exercise. To minimize epidermal and skin surface contamination, the subjects were requested to thorough shower right before exercise, and not to apply any skin care products on their skin, especially face and neck. Sweat samples were collected off the skin of subjects' face and neck directly into 1.5 ml Eppendorf LoBind microcentrifuge tubes. Collected sweat samples were pooled and transferred to dry ice immediately at site of collection, and subsequently to −80° C. freezer until use. Immediately before use, sweat samples were thawed and centrifuged at 4° C. for 10 minutes at 16000 rcf in an Eppendorf 5415 centrifuge to remove any potential debris/particles off the skin during sweat collection.
Sample Extraction Procedure
For standards and controls: 50 µl of the calibration standards or controls, 10 µl of the IS working solution (250 ng/ml in 10% acetonitrile), 200 μl artificial sweat and 200 μl 0.1 M ammonium acetate pH 5.5 were mixed in a 2 ml microcentrifuge tube. The mixture was vortexed and 1 ml of ethyl acetate was added, followed by vortex and centrifuge at 12600 rcf at 4° C. for 10 minutes. The upper organic layer was transferred to glass test tube. The ethyl acetate extraction was repeated twice and organic layer was combined in test tube. The organic solvent was then evaporated to dryness in a centrifugal evaporator (SpeedVac, Thermo Fisher, Milford, Mass.). The dry residues were reconstituted with 100 μl 10% acetonitrile and transferred to autosampler vials, where 50 μl were injected into HPLC-MS system for analysis.

For human sweat samples: 200 μl sweat samples were mixed with 50 μl 10% acetonitrile, 200 μl 0.1 M ammonium acetate pH 5.5 and 10 μl internal standard working solution in a 2 ml microcentrifuge tube, followed by the same extraction procedure as the standard solutions above.

UPLC-Mass spectrometry

The HPLC-MS/MS system consisted of a Waters Acquity iClass UPLC system and a Waters Xevo G2-S QTOF mass spectrometer (Waters Corporation, Milford, Mass.). A Waters Micromass Quatro Premier XE QqQ was also employed for targeted MRM analysis. An Acquity UPLC BEH C-18 column (1.7 μm, 2.1×50 mm, Waters Corporation, Milford, Mass.) or a Restek Ultra II aromax column (1.9 um, 2.1×50 mm) was used for separation with binary gradient elution. Mobile phase A consisted 0.1% formic acid in water, and mobile phase B consisted 0.1% formic acid in acetonitrile. Flow rate was 250 μl/min with the following gradient: 0% B (0-2.0 min), from 2% to 40% B (2.0-12 min), from 40% B to 0% B (12-12.1 min), 100% B (12.1-15 min). Temperature of column oven was 30° C. Sample vials were maintained at 10° C. in the autosampler tray.

On the QTOF, ionization of the mass spectrometry analysis was electrospray ionization (ESI) operated in positive ion mode, with a capillary voltage of 2560V. The source and desolvation temperature was 140° C. and 400° C., respectively. Drying gas (nitrogen) flow rate was 700 L/hr. Data was collected from 50-1200 Daltons. Mass correction is done using leucine enkephalin as the reference compound. Instruments are controlled by MassLynx software.

Stability of Cortisol in Human Eccrine Sweat

To test the stability of cortisol in human eccrine sweat in order to improve sweat collection method and procedures, aliquots of the same sweat samples were left at room temperature for a duration of 3 hours, with each aliquots analyzed every 30 minutes in first hour and every hour afterwards.

Method Validation

The calibration standards were prepared on each analysis day from a single batch of cortisol working solutions. The linearity of the detection was evaluated with single measurement of spiked artificial sweat sample, zero (artificial sweat spiked with IS) and each of the 6 standards with concentration from 0.05 to 25.00 ng/ml.

The within-day and between-day variations were also evaluated via spiking 0.63 and 20.00 ng/ml of cortisol into aliquots of artificial sweat samples. 5 measurements for each concentration were performed within a validation batch for within-day variation assessment. This analysis was repeated over a 3-day period for between-day variation assessment. The concentrations of the QC standards were determined from the calibration curve prepared for each day. The RSD of the concentration determined within a run (5 replicates) and among 3 runs were used to show the within-day and between-day precision of the method, respectively.

The percent difference between measured and theoretical concentrations within a run and among 3 runs were used to determine within-day and between-day accuracy of the method, respectively.

The extraction recovery of cortisol was determined by comparing the peak areas for the quality control standards spiked before extraction to peak areas for standards spiked after extraction. Matrix effect was evaluated by comparing the peak areas for the quality control standards spiked after extraction to peak areas for standards in 10% acetonitrile. Recovery of cortisol in human eccrine sweat was also examined by calculating the ratios of the peak areas for sweat samples to peak areas for spiked sweat samples using the below equation:

$$\% \ R = 100 \times \frac{Msp - Mo}{Mt} \quad (1)$$

Where % R represents percent recovery, Msp represents the total amount of cortisol detected in spiked sweat sample aliquot; Mo represents the amount of cortisol in original sweat sample aliquot, and Mt represents the theoretical amount spiked.

Results and Discussion

Identification of Cortisol Isomers in Sweat

Figure 13:
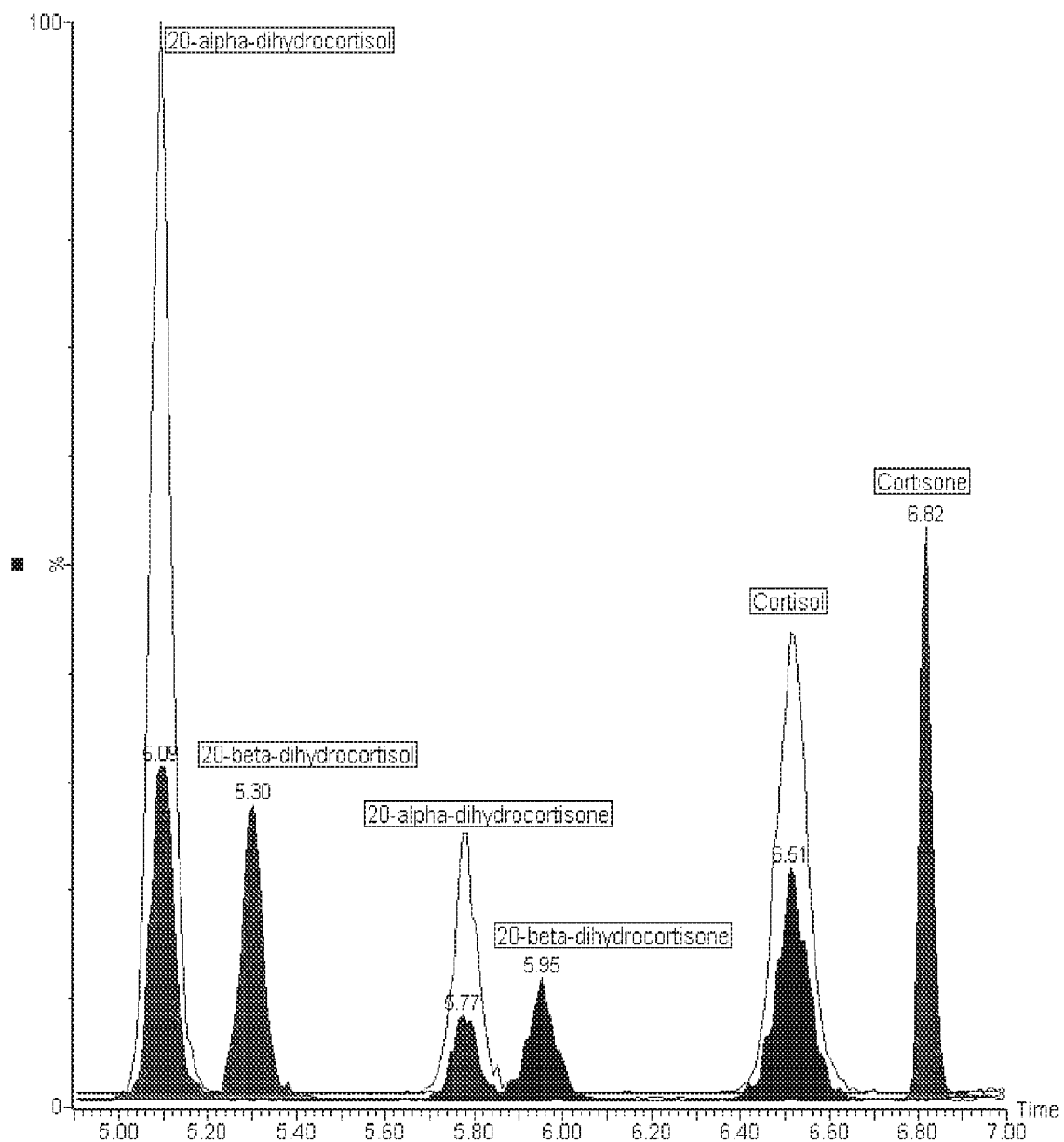
FIG. 13. Mass spectrometry chromatogram of standard mixture of cortisol, cortisone, 20α-dihydrocortisone, and 20β-dihydrocortisone, 20α-dihydrocortisol, 20β-dihydrocortisol (QQQ, Total Ion Chromatogram, TIC)
Figure 15:
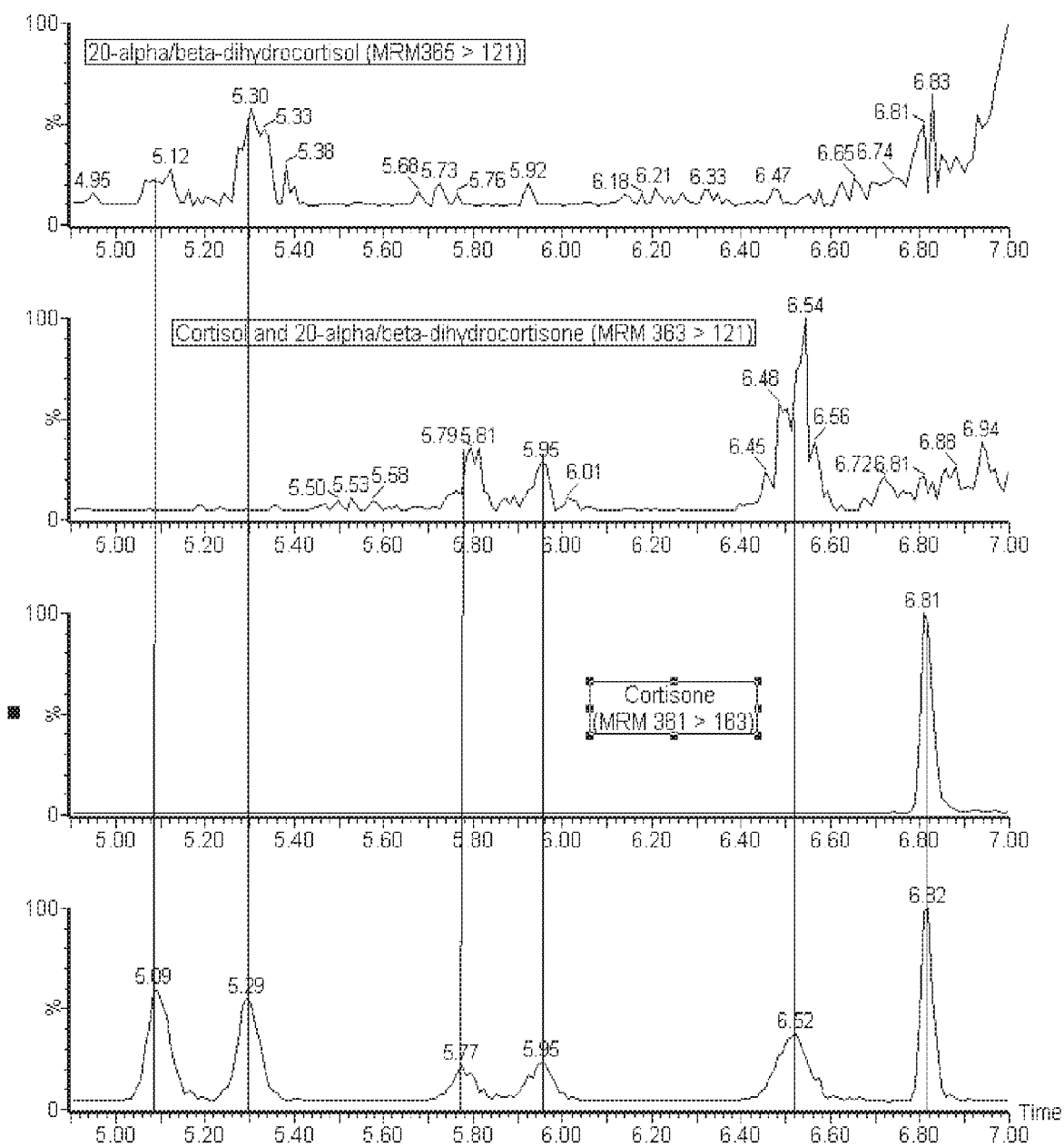
FIG. 15. Mass spectrometry chromatogram of a typical human eccrine sweat sample indicating the presence of cortisone, 20α-dihydrocortisone, and 20β-dihydrocortisone, 20α-dihydrocortisol, 20β-dihydrocortisol (QQQ, EIC). The identification was achieved via characteristic MRM transitions for each cortisol metabolites and isomers, as well as the characteristic retention time of each molecular species.

In previous work of quantifying cortisol in human eccrine sweat using LC-MS/MS (QQQ), experiments discovered two cortisol isomers in sweat. Under positive APCI conditions, these isomers share similar typical MRM transitions with cortisol (363→121, dipole ions; 363→327, -2H2O). m/z 163 is a typical major fragment ion from cortisone where there is a carbonyl group at C11. The cortisol isomers also possess a 363→163 transition, which was not significant for cortisol fragmentation under the same MS conditions. This indicates that a carbonyl group is probably present on C11 of these isomers, i.e., these isomers are most likely dihydrocortisone. Based on this preliminary evidence, three commercially available standard dihydrocortisone isomers were obtained: 20α, 20β dihydrocortisone. These standards were monitored with a 0.02 Da (10 ppm) mass window for cortisol, cortisone, and the 4 cortisol isomers. Other than exact mass, retention times of the standards were compared to the chromatogram of sweat samples under the same conditions to identify the species of the isomers. FIG. 2-12 indicated the identification process of cortisol and its two isomers in eccrine sweat samples, based on exact mass, retention time and spike experiments. FIG. 13 is a typical chromatogram for the separation of cortisone, cortisol and related metabolites. FIG. 15 is a typical chromatogram for the separation of sweat samples under the same conditions, indicating the same retention times for certain standard glucocorticoid species as compared to the isomers we observed in human eccrine sweat samples. As expected, the two cortisol isomers appear to be 20α and 20β dihydrocortisone. Matching MRM transitions and retention times with standard compounds further confirmed the identity of the isomer and metabolite species to be 20 α/β dihydrocortisone, and 20 α/β-dihydrocortisol.

Sweat Pretreatment

Sweat is a relatively new source biofluid for biomarker analysis using HPLC-MS/MS. In this study, three sweat cleanup and preparation methods were tested in order to develop a simple and efficient sample processing method for accurate analysis of cortisol. In method 1, sweat samples were simply centrifuged at 12600 rcf at 4° C. for 10 minutes, then the supernatant was injected into HPLC for analysis. This method suffered from repeatability problem, indicating there could be ion suppression/matrix effect even when cortisol-d4 was co-eluted with cortisol, which theoretically should be able to "correct" the effect of ion suppression and matrix effects. A post column infusion experiment indicated that there is no observable ion suppression at the time of cortisol elution, therefore the analysis variation was not caused by matrix effect. Cortisol is known to be binding to serum albumin, and albumin was reported to be the most abundant protein in human eccrine sweat. Different degree of binding/unbinding in mobile phase during HPLC separation might be a possible reason for the observed reproducibility problem. In method 2, sweat samples were filtered through 0.2 μm EMD microfiltration membranes, then the filtrate was injected into HPLC for analysis. The major problem with this method is the loss of cortisol during filtration. Due to the low concentration of cortisol in sweat, non-specific binding of cortisol to the membrane could be significant. A liquid-liquid extraction procedure using ethyl acetate (as described in Experimental Section) therefore was developed to address the above problems. The extraction recovery averaged at 107% was obtained, indicating the necessity of using proper extraction method in sweat cortisol analysis when employing HPLC-tandem mass spectrometry analysis. A comparison of the extraction recovery was shown in Table 1.

Stability Test of Cortisol in Human Eccrine Sweat

Sweat collection normally takes time to complete, especially at low sweat rate. A key question is whether cortisol is stable in sweat, and if not, how to determine the degradation rate and develop sweat collection and preprocessing methods to minimize cortisol loss in sweat due to degradation. This is a critical procedure in order for a reliable analysis of sweat cortisol. Spiked human eccrine sweat samples were tested over a period of 3 hours at room temperature. No measurable cortisol loss was observed during this time period, indicating that sweat cortisol is stable under experimental conditions, as shown in Table 1.

Method Validation

Cortisol was used as a model compound. Sweat cortisol calibration curves were constructed using the ratios of the peak area of cortisol to cortisol-d4 versus cortisol concentrations in artificial sweat samples. Linear least-squared regression with a weighting factor of 1/y was used for curve fitting. Linear range was found to be from 0.1 ng/ml to 25 ng/ml. The lower limit of quantitation (LLOQ) is defined as the concentration corresponding to 10 times of the blank signal, with a RSD of less than 20% and an accuracy of 80-120% of nominal concentration. The Lower limit of detection (LLOD) is defined as the lowest concentration that showed a peak response 3 times compared to bank signal. Based on these definitions, the LLOD and LLOQ were estimated to be ~0.04 ng/ml and ~0.1 ng/ml.

Table 3 below listed the method accuracy, precision and extraction recovery. Within-day analysis evaluated accuracy and precision during a single analytical run of 5 replicates for each QC sample. The concentrations of these QC samples were determined by using a calibration curve prepared for each batch. The between-day accuracy and precision were determined from 3 analytical runs of 5 replicates for each QC sample over three days. The concentrations of these QC samples were determined by a calibration prepared each day. The within-day % RSD and % difference were from 2.5 to 9.7 and from 0.5 to 2.1, respectively. The between-day % RSD and % difference were from 12.3 to 18.7 and from 7.1 to 15.1, respectively. Extraction recoveries for cortisol and for the IS were between 90% and 110%.

Although theoretically the matrix effect should be largely minimized with the use of stable isotope labeled internal standard, possible ion suppression was also tested using post column infusion method. In this experiment, due to the lack of genuine "blank human eccrine sweat", we used simulated sweat in place of blank sweat samples. No ion suppression was observed at around the retention times of cortisol as well as its isomers. The recovery of sweat cortisol analysis may also be used as one quick and easy way to detect the presence or lack of matrix effects. As indicated in Table 1, close to 100% recovery of cortisol in eccrine sweat was obtained using the liquid-liquid extraction method, which confirms the lack of matrix effects in the developed method.

Application to Human Eccrine Sweat Cortisol Analysis

Using cortisol as a model compound, the optimized method was successfully applied to the sensitive analysis of cortisol in human eccrine sweat. Sweat samples were collected from a volunteer in a hot chamber during two sessions in the same day: 1 pm to 1:30 pm and 4 pm to 4:25 pm. Plasma cortisol levels are known to undergo diurnal effect with highest concentrations at wakeup and lowest at late night. Data in Table 4 showing lower sweat cortisol levels at 4 pm than those at 1 pm. This trend is in accordance with plasma cortisol circadian cycle. It was noted that multiple factors other than stress could affect sweat cortisol concentrations: sweat rate, body location of sweat collection, food intake, physical exercise and hydration levels, therefore caution was used to minimize the possible cortisol variations caused by these factors.

The sweat concentrations we obtained using HPLC-MS/MS were much smaller than the results from the previous ELISA analysis of human eccrine sweat. In this ELISA study, an average of 74.62±41.51 ng/mL sweat cortisol was obtained, with concentration ranged from 8.16-141.7 ng/mL. This time course of cortisol levels agrees with our findings using HPLC-MS/MS: lower in evening and higher in morning, collection period 7:40 am to 22:00 pm. These results are much higher as compared to our results of 2.80-0.24 ng/ml using LC-SRM from 1 pm to 4 pm. There are several possible reasons for this discrepancy. First, EIA of cortisol and other steroids are known to have significant cross-reaction with polar markers with known or unknown structures, which leads to false positives. We believe this is also true for a previous study (Ther Drug Monit. 2014 February; 36(1):30-4.), especially considering that sweat is a novel biofluids for cortisol analysis and its composition of steroid markers are largely unknown. Second, in the Ther Drug Monit study, the sweat samples were collected soon after the subjects underwent intense exercise. It was reported before that medium to high intensity exercise provokes increasing circulating cortisol levels [J Endocrinol Invest. 2008 July; 31(7):587-91]. The percent change of post exercise cortisol increase in plasma was reported to be less than 90%, therefore, the high cortisol concentrations observed in the previous study could not be mainly attributed to the effect of physical activities. Rather, it is more likely that other matrix components, including other steroids, markers, drugs or as we shown in this study, also structurally similar isomers that are responsible for the high sweat cortisol concentration levels observed in human sweat.

Analysis of Cortisol, Cortisone, 20α-DHE, 20β-DHE, 20α DHF and 20β DHF in Sweat 6 eccrine sweat samples were collected from 3 healthy subjects during a 1-hour heat session (40° C.). One sweat sample was collected at ~40 minutes while a 2nd sample collected at ~60 minutes for each subject. Use UPLC-QQQ (MRM), cortisol, cortisone, 20α-DHE, 20β-DHE, 20α-DHF and 20β-DHF were analyzed. Due to the sensitivity limitation posed by the aged Waters Micromass Quattro Premier QQQ, only cortisol, cortisone and the cortisol isomer 20α-DHE achieved well above S/N 10 for quantitation. Data in table 5 showing the increase of both cortisol and 20α-DHE at ~60 minutes as compared to 40 minutes while cortisone levels are mostly constant. The cortisol/cortisone (F/E), 20α-DHE/cortisone (20α-DHE/E) ratios are also increased in samples collected at 60 minutes as compared to 40 minutes. Currently, cortisol/cortisone (F/E) ratio is widely used in clinical lab as a screening test for Cushing syndrome (hypercortisolism), stress and depression levels. This data indicates that the cortisol isomer 20α-DHE also increases as stress levels increases. Therefore, as indicated in Table 5, while technically the detection of additional isomers/metabolites such as 20α-DHE with LC-MS/MS poses no additional time and only minimal additional cost, an immediate benefit is that the ratio (F+20α-DHE)/E will provide more sensitive measure of stress levels as compared to only use F/E ratio. More sensitive marker response to stress levels or stress related disorders will lead to more specific and accurate diagnosis of such disorders in clinical lab.

This data indicated the potential of using these isomers/metabolites as additional or novel biomarkers to serve as effective markers for stress and stress-related disorders. Other markers, 20β-DHE, 20α-DHF and 20β-DHF, will also be quantified (with, for example, the Thermo Quantiva 2016 model) with higher sensitivity in near future. Clinical studies with much larger sample size and number of subjects will also be conducted to establish correlations of absolute or relative levels of markers with stress levels.

CONCLUSIONS

Using UPLC-QTOF and/or UHPLC-QQQ, experiments identified and quantified cortisol and related metabolites that are found for the first time in human eccrine sweat. In addition to cortisol, a total of 5 cortisol metabolites were found: cortisone, 20α-DHE, 20β-DHE, 20α-DHF and 20β-DHF. The relative abundance of these metabolites/isomers are different among different individuals. Preliminary data indicated that differences in relative abundance of these markers were also observed in the same subject correlating with different stress levels (different time points during heat stress session), strongly suggests that these markers be promising markers for non-invasive measurement of stress levels.

TABLE 1

Comparison of different sweat extraction methods

| Sample Prep Method: | 1. Centrifuge + vacuum dry | 2. Filtering with 0.2 micro + vacuum dry | 3. Acetonitrile + ethyl acetate + centrifuge + vacuum dry |
|---|---|---|---|
| Spiking Recovery: | 80% | 25%–40% | 107% |
| Problems: | reproducibility | Analyte loss, reproducibility | N/A |

TABLE 2

Stability of cortisol in human eccrine sweat at room temperature

| Time | Concentration (ng/ml) |
|---|---|
| unspiked | 3.488 |
| spiked 0 minutes | 29.191 |
| spiked 30 minutes | 36.802 |
| spiked 1 hour | 30.807 |
| spiked 2 hours | 30.228 |
| spiked 3 hours | 29.515 |

TABLE 3

Accuracy and Precision of the method

| | Theoretical Cortisol Concentrations (ng/ml) | |
|---|---|---|
| | 20.000 | 0.625 |
| Within Day | | |
| Mean Measured Concentration (n = 5) | 20.422 | 0.628 |
| Standard Deviation | 0.504 | 0.061 |
| Precision (% RSD) | 2.5% | 9.7% |
| Accuracy (% difference) | 2.1% | 0.5% |
| Between Day | | |
| Mean Measured Concentration (n = 15) | 21.420 | 0.531 |
| Standard Deviation | 2.631 | 0.099 |
| Precision (% RSD) | 12.3% | 18.7% |
| Accuracy (% difference) | 7.1% | −15.1% |
| Extraction Recovery (%, n = 5) | 97 | 103 |

Precision is expressed as % RSD.: (standard deviation)/(mean measured concentration) × 100
Accuracy is expressed as % difference: [(measured − theoretical conc)/theoretical conc] × 100.

TABLE 4

Cortisol levels in human eccrine sweat collected at different times of the day

| Collection Time | 1-1:30 pm | 4-4:30 pm |
|---|---|---|
| Concentration (ng/ml) | 1.832 | 0.686 |
| | 1.829 | 0.736 |
| | 1.746 | 0.342 |
| | 1.626 | 0.240 |
| | 1.953 | 0.340 |
| | 1.068 | 0.507 |
| | 1.215 | 0.670 |
| | 2.802 | |
| | 1.470 | |
| | 1.307 | |
| Average Concentration (ng/ml) | 1.68 ± 0.49 | 0.50 ± 0.20 |

TABLE 5

Quantitation of cortisol, isomers and metabolites in sweat

| | corti-sol(F) | corti-sone(E) | 20aDE | F/E | 20DE/E | (F + 20DE)/E | F/20DE |
|---|---|---|---|---|---|---|---|
| S1 40 min | 3.11 | 13.30 | 2.80 | 0.23 | 0.21 | 0.44 | 1.11 |
| S1 60 min | 5.62 | 15.39 | 3.41 | 0.37 | 0.22 | 0.59 | 1.65 |
| S2 40 min | 6.28 | 18.90 | 2.87 | 0.33 | 0.15 | 0.48 | 2.19 |
| S2 60 min | 8.07 | 18.23 | 3.67 | 0.44 | 0.20 | 0.64 | 2.20 |
| S3 40 min | 2.62 | 10.49 | 3.14 | 0.25 | 0.30 | 0.55 | 0.83 |
| S3 60 min | 3.31 | 11.16 | 3.73 | 0.30 | 0.33 | 0.63 | 0.89 |

Example 2

The aforementioned new cortisol isomers in sweat, which are similar or identical to ones found in placenta, are ordinarily produced by an enzyme that is induced by stress levels of cortisol.

The stress hormone cortisol is a small steroid hormone (MW: 362.46) that plays many important roles in physiological and psychological processes. It is secreted by the adrenal glands, as an end product of the hypothalamic-pituitary-adrenal (HPA) axis cascade mainly in response to stress or fear in surrounding environments. Cortisol is crucial for homeostatic maintenance, by means of modulating, regulating or influencing vital systems including neural, immune, cardiovascular, metabolic, and endocrine systems. Abnormal circulating cortisol levels can lead to illness. Prolonged elevated levels are associated with impaired cognitive performance, hyperglycemia, sleep disruption, elevated blood pressure, suppressed immune function, obesity, fatigue; and contribute to the development of Cushing's disease. Cortisol is therefore a useful biomarker in many stress-related conditions.

The current state of the art for cortisol measurement relies on plasma, saliva or urine as the biological fluid in which cortisol is measured. One drawback of using plasma cortisol levels as a marker of stress is that the act of drawing blood is in itself stressful, and can therefore cause elevations in measured cortisol. Another drawback is that a single measure of cortisol reflects the acute stress response at any given point in time, and is not reflective of chronic stress or total stress over a 24-hour period. Furthermore, a single plasma cortisol is only indicative of acute stress at that moment of collection. In order to accurately estimate cortisol total exposure, areas under the curve from multiple blood draws or continuous sampling must be used to calculate total cortisol secreted over a given time period. Furthermore, circadian fluctuations in cortisol levels, with peak levels in the morning and nadirs in the evening must also be taken into account and require multiple blood draws or continuous sampling. 24-hour urine collection, while providing an indication of 24-hour cortisol levels, is cumbersome to collect, and often unreliable as a result of incomplete collections. Saliva is easy to collect however, the necessity of collecting multiple samples throughout the day is also cumbersome and adds to subject burden. A different biological fluid as a source for measuring cortisol would therefore help to overcome these drawbacks. As sweat is easily accessible and has the potential for non-invasive continuous monitoring, it provides an ideal sample for measurement of biomarkers in a non-invasive manner.

A variety of biomarkers are detectable in sweat and that patterns and levels of sweat biomarkers correlate with plasma levels [J. Immunol. Methods, 2006, 315:99-109; Anal Chem. 2012 Aug. 7; 84(15):6508-14], as well as with symptoms in women with a history of major depressive disorder [Biol Psychiatry. 2008 Nov. 15; 64(10):907-11].

Based on the HPLC-MS/MS results presented, the structure of these isomers in sweat was shown to be the same as the 20-dihydrocortisone isomers present in placenta perfusate samples (Analytical Biochemistry, 247, 342-347 (1997)). The similarity of the chemical profile of the new sweat cortisol isomers with those found in placenta provides information on their physiological relevance in sweat. Maternal glucocorticoids, especially cortisol, can have an adverse effect on the fetus. Therefore, tight regulation of fetal cortisol exposure is an important regulatory process to maintain a healthy physiological status for the fetus. Cortisol metabolizing enzymes in placenta can protect the fetus from elevated blood pressure levels related to elevated circulating cortisol, a process that is important for the baby's health and growth. As a result, the circulating concentration of active cortisol in a fetus is much lower than it is in the mother. One route by which the fetus is protected from elevated maternal circulating cortisol is via degradation of the active hormone, cortisol, by placental cortisol catabolizing enzymes. One such enzyme is 11-beta-hydroxylsteroid dehydrogenase (11betaHSD), which converts hormonally active cortisol to inactive cortisone. 11betaHSD has also been identified in adult sweat gland ducts, and impaired 11betaHSD sweat gland duct activity has been reported in human essential hypertension (Hypertension, 2004, 43(4), 803-808). These findings indicated a similarity in stress regulations in placenta and sweat glands. The findings of two cortisol isomers (20α-dihydrocortisone, and 20β-dihydrocortisone) and 20α-dihydrocortisol, 20β-dihydrocortisol in human sweat indicate the presence of new metabolic pathways that may be different from the 11betaHSD and 3a, 20β-Hydroxysteroid Dehydrogenase route.

Given the importance that placental cortisol metabolizing enzymes play in maintenance of fetal cortisol and physiologic homeostasis, it is contemplated that the presence of the new isomers and metabolites that we have identified in sweat may indicate a similar cortisol homeostatic mechanism in skin, sweat glands, or sweat. We further claim such regulation plays a role in protection from elevated stress levels of cortisol, and as such the ratios of the new cortisol markers to cortisol are a useful novel biomarker for stress levels and homeostasis.

The amount of the two new cortisol isomers and metabolites we found in human eccrine sweat is substantial, and is comparable to that of active cortisol in sweat. The presence of two cortisol isomers and metabolites in human eccrine sweat indicates that there could be different, direct or indirect enzymatic routes for cortisol conversion in human sweat.

Using bioanalytical chemistry techniques, we identified the structure of the cortisol isomers, metabolites and will establish the correlation of these cortisol isomers identified in placenta and sweat; also investigate skin/sweat gland metabolizing enzyme(s) and mechanisms that may be involved in producing the sweat cortisol markers that we have identified.

Figure 14:
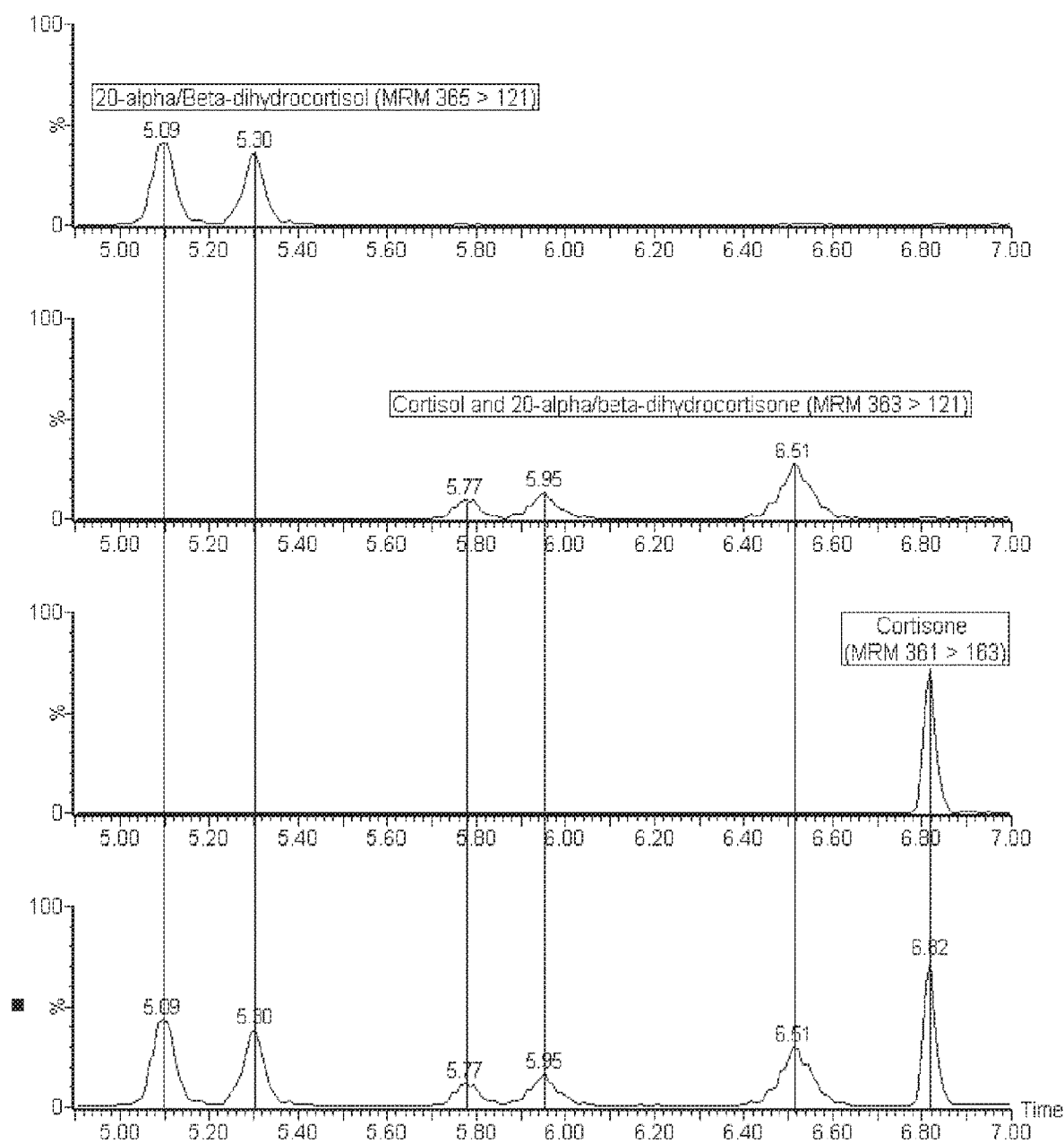
FIG. 14. Mass spectrometry chromatogram of standard mixture of cortisol, cortisone, 20α-dihydrocortisone, and 20β-dihydrocortisone, 20α-dihydrocortisol, 20β-dihydrocortisol (QQQ, EIC), indicating characteristic MRM transitions for each cortisol metabolites and isomers.

Using a mixed mode SIELC Primesep 100A column, complete separation of cortisol and its two isomers was achieved. FIG. 1 showed the complete separation of the three molecules, indicating the presence of two isomers in human eccrine sweat. FIG. 13-15 showed the complete separation of all 6 cortisol related markers using a Waters BEH C18 UPLC column, indicating the presence of all 6 cortisol related markers in human eccrine sweat.

Placental tissue samples are prepared and cortisol and its isomers are isolated from human placental tissue and human eccrine sweat using solid phase extraction to ensure the most specific sample cleanup and concentration.

The cortisol isomers are separated and characterized by high performance liquid chromatography—high accuracy mass spectrometry (e.g., Q-TOF MS, QqQ or LTQ Orbitrap). The results obtained from high resolution QTOF and MRM MS analysis of cortisol isomers and metabolites for placental samples are compared to those in sweat: cortisol, cortisone, 20α-dihydrocortisone, and 20β-dihydrocortisone, 20α-dihydrocortisol, 20β-dihydrocortisol.

In this example, the invention has important and broad applications in adult and fetal medicine, and in particular as a potential new biomarker for stress and resilience. It would also be a theoretical breakthrough should we discover a novel enzymatic pathway for cortisol metabolism in placenta and sweat glands, therefore adding new knowledge regarding the roles of sweat glands and their involvement in stress regulation.

Example 3

Figure 3:
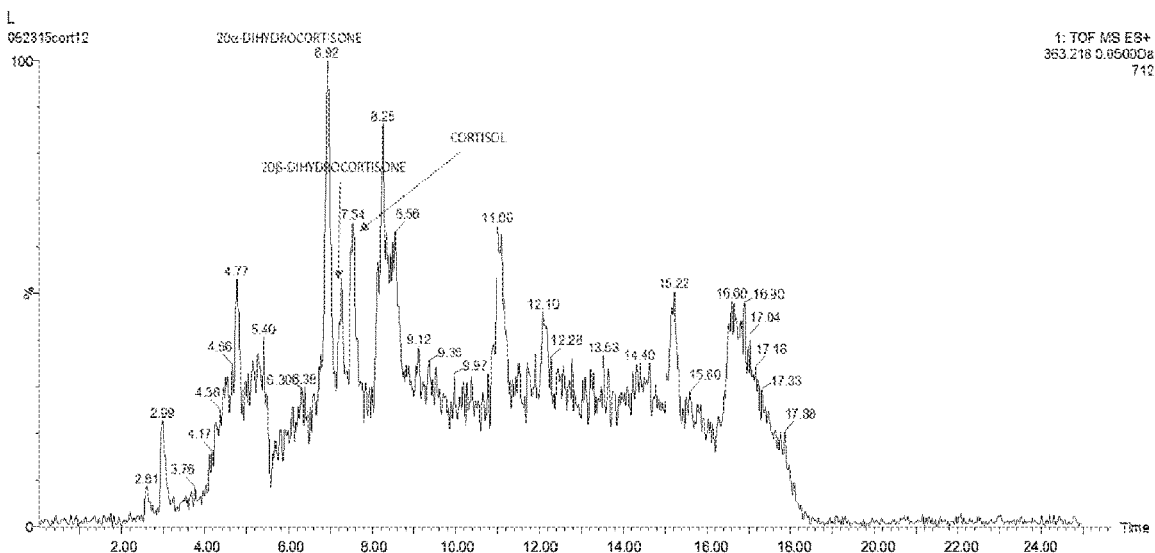
FIG. 3. Mass spectrometry chromatogram showing cortisol and 20α-dihydrocortisone and 20β-dihydrocortisone isomers in human sweat (QTOF).
Figure 4:
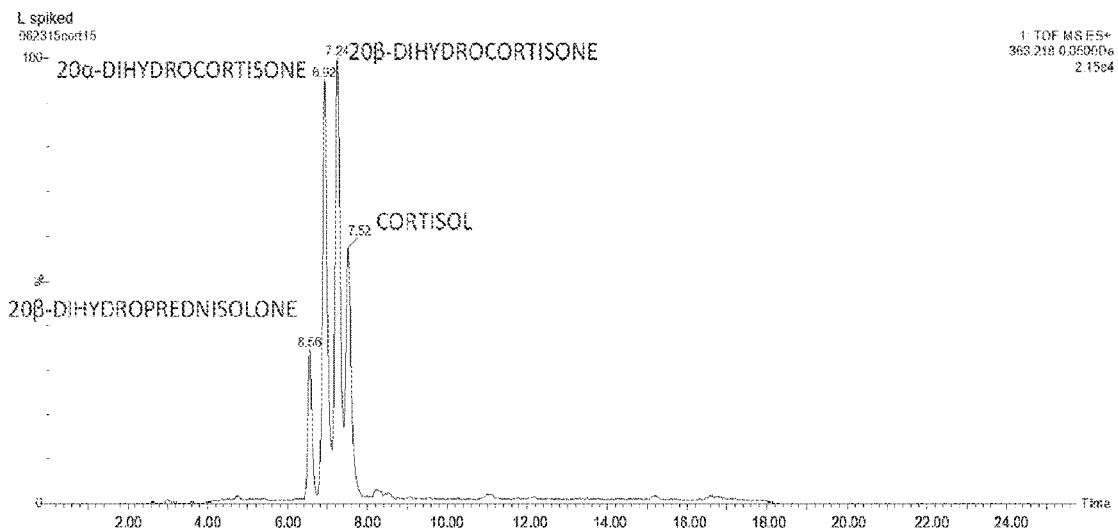
FIG. 4. Mass spectrometry chromatogram showing cortisol and 20α-dihydrocortisone and 20β-dihydrocortisone isomers in human sweat spiked with 20α-dihydrocortisone and 20β-dihydrocortisone standards (QTOF).
Figure 5:
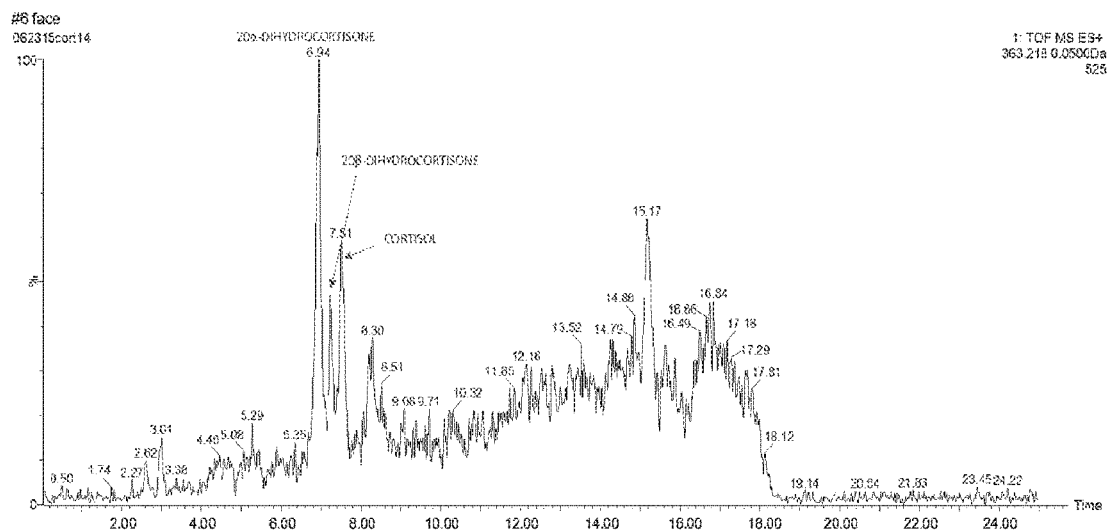
FIG. 5. Mass spectrometry chromatogram showing cortisol and 20α-dihydrocortisone and 20β-dihydrocortisone isomers in human sweat (QTOF).
Figure 6:
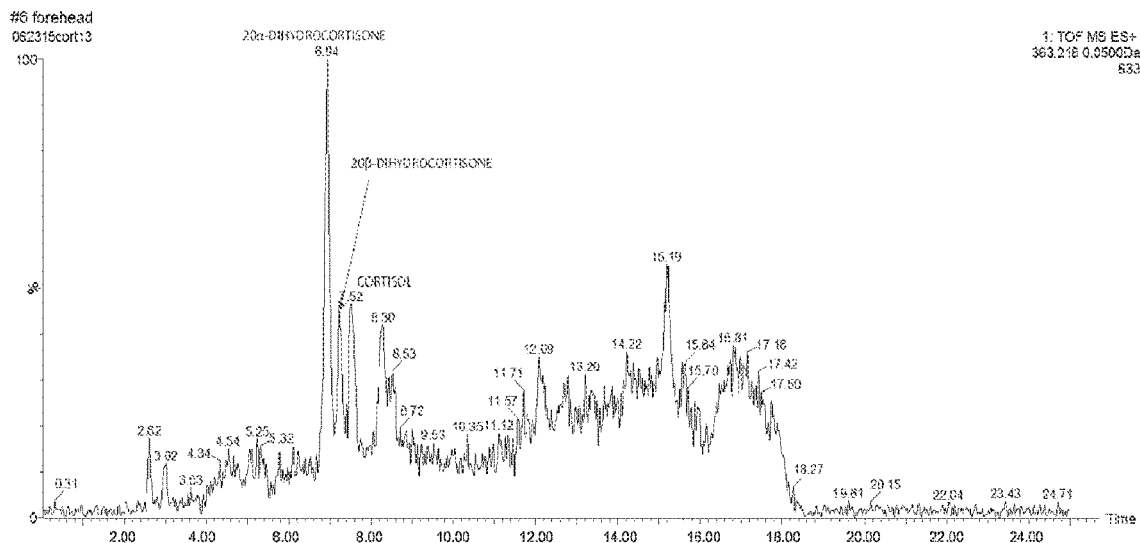
FIG. 6. Mass spectrometry chromatogram showing cortisol and 20α-dihydrocortisone and 20β-dihydrocortisone isomers in human sweat (QTOF).
Figure 7:
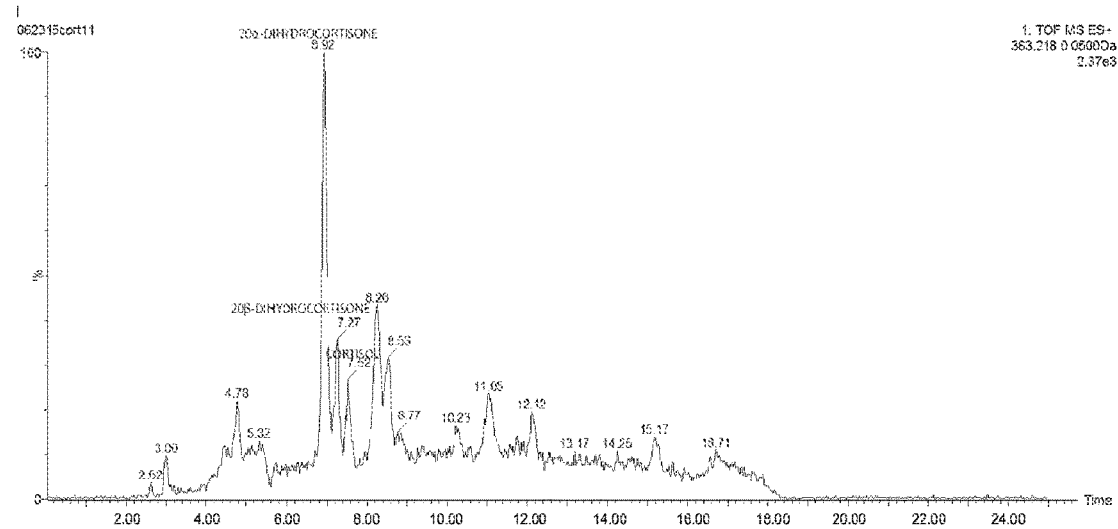
FIG. 7. Mass spectrometry chromatogram showing cortisol and 20α-dihydrocortisone and 20β-dihydrocortisone isomers in human sweat (QTOF).
Figure 8:
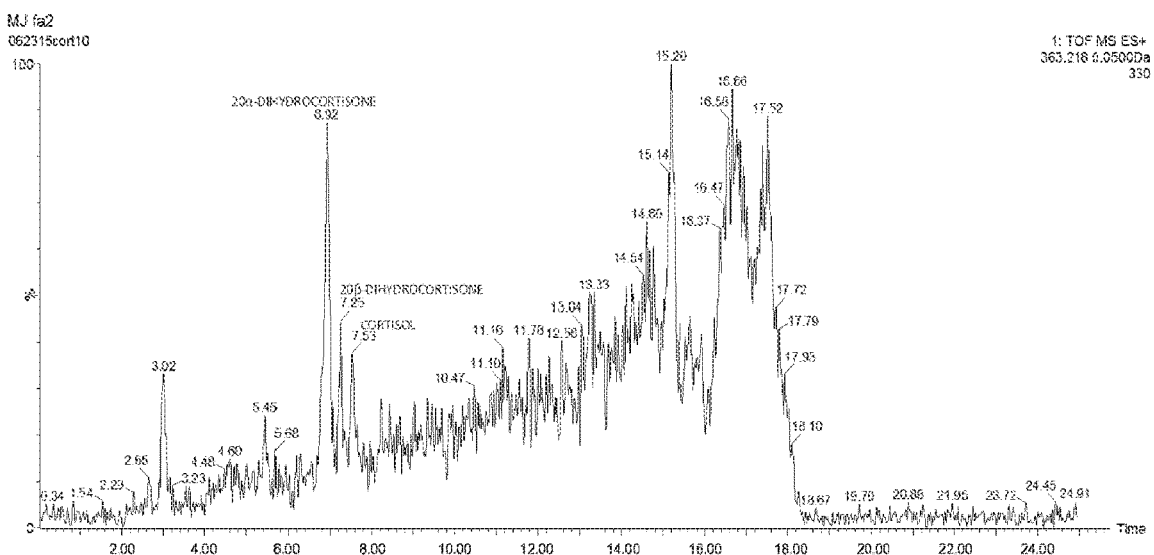
FIG. 8. Mass spectrometry chromatogram showing cortisol and 20α-dihydrocortisone and 20β-dihydrocortisone isomers in human sweat (QTOF).
Figure 9:
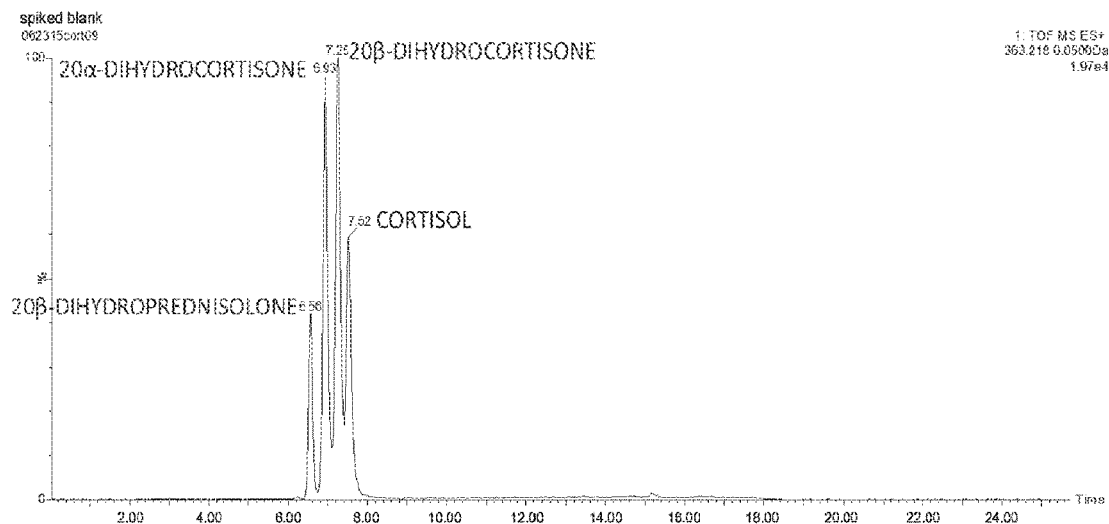
FIG. 9. Mass spectrometry chromatogram of a blank sample spiked with cortisol and 20α-dihydrocortisone and 20β-dihydrocortisone isomers (QTOF).
Figure 10:
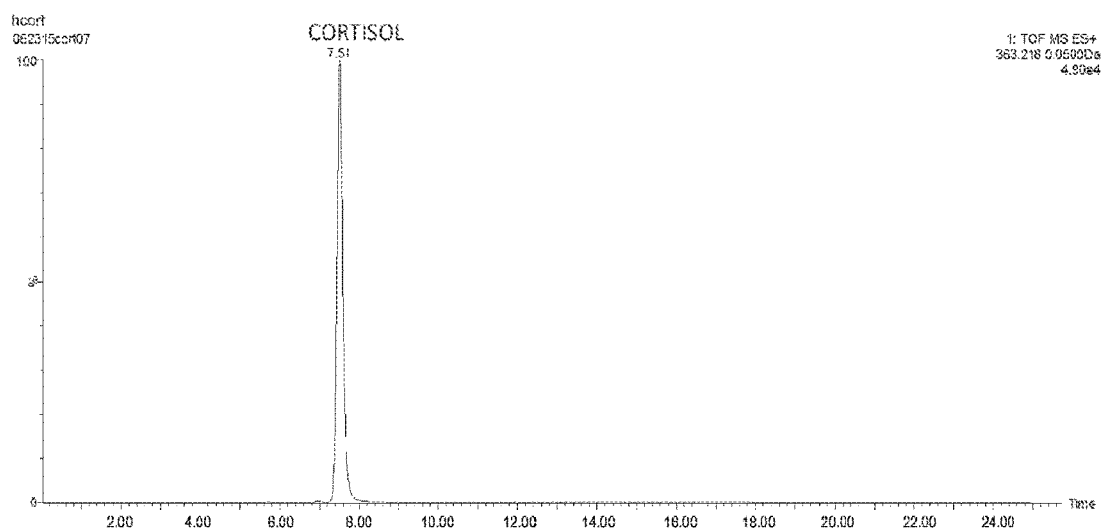
FIG. 10. Mass spectrometry chromatogram of cortisol (QTOF).
Figure 11:
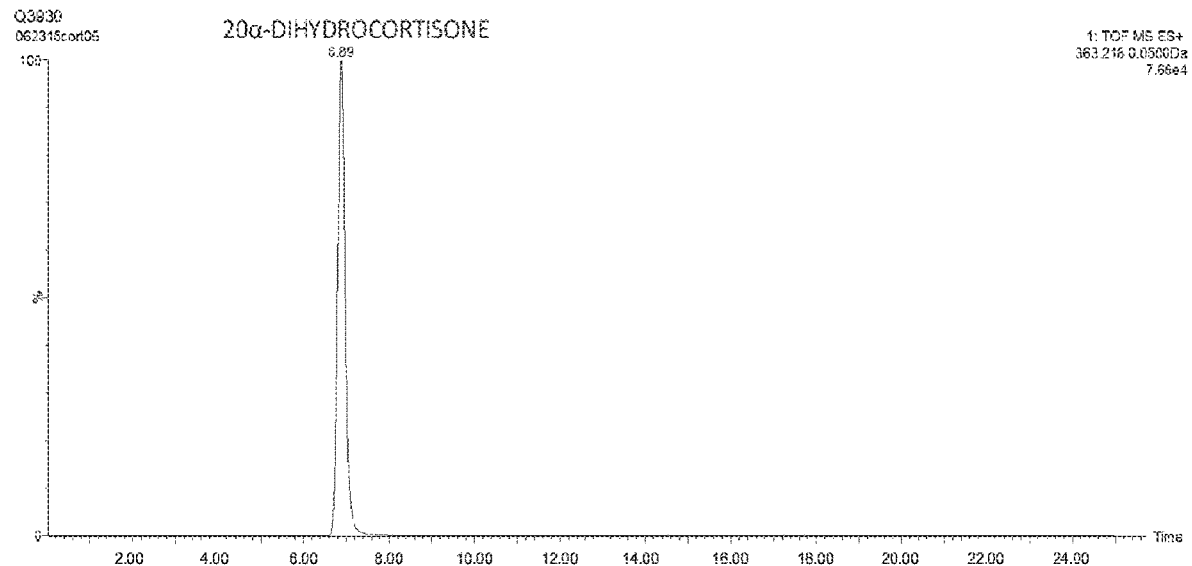
FIG. 11. Mass spectrometry chromatogram of 20α-dihydrocortisone (QTOF).
Figure 12:
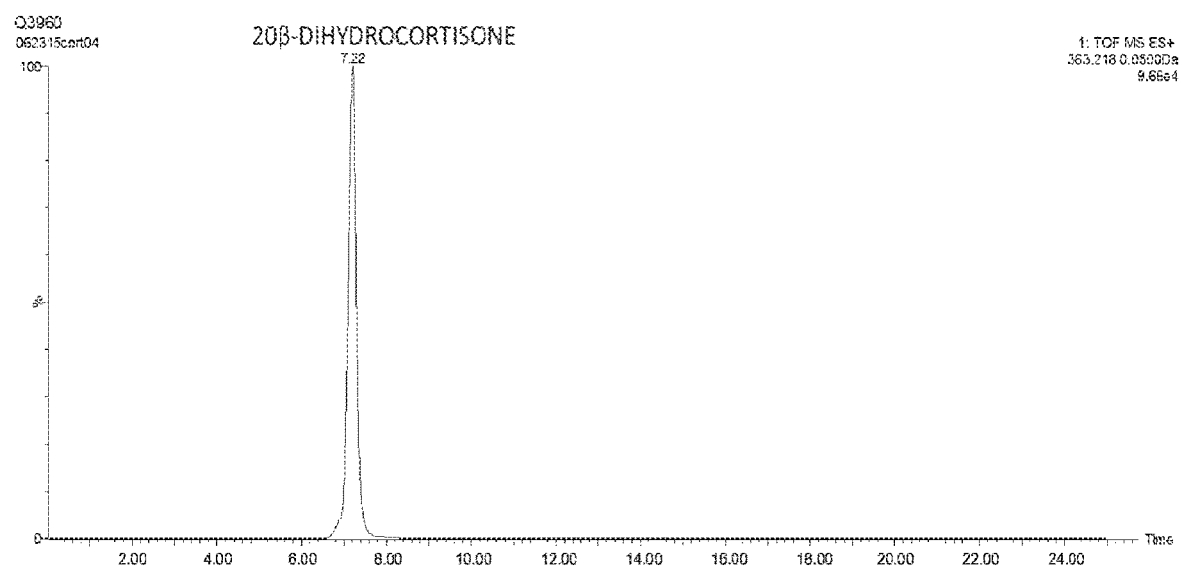
FIG. 12. Mass spectrometry chromatogram of 20β-dihydrocortisone (QTOF).

HPLC-MS retentions time of known standard cortisol isomers were compared with the retention times of the isomers found in sweat. Results are shown in FIGS. 3-15. FIGS. 3-4 show a spiked sweat sample L with known standard isomers. The resulting increase of peaks at the same retention times was shown. These data indicate that the isomers in sweat are 20α-dihydrocortisone and 20β-dihydrocortisone. FIG. 13-15 indicated the presence of cortisol, cortisone, 20α-dihydrocortisone, and 20β-dihydrocortisone, 20α-dihydrocortisol, 20β-dihydrocortisol in human eccrine sweat, where unique MRM transitions and chromatogram retention times were used to identify these markers.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments.

Indeed, various modifications and variations of the described compositions and methods of the invention will be apparent to those of ordinary skill in the art and are intended to be within the scope of the following claims.

We claim:

1. A method, comprising:
   obtaining a sweat sample from a human subject;
   performing mixed-mode RP-HPLC to separate cortisol, 20α-dihydrocortisol, 20β-dihydrocortisol, cortisone, 20α-dihydrocortisone, and 20β-dihydrocortisone from the sweat sample; and
   quantifying the amount of the separated cortisol, 20α-dihydrocortisol, 20β-dihydrocortisol, cortisone, 20α-dihydrocortisone, and 20β-dihydrocortisone from the sweat sample through use of MS-MS.

2. The method of claim 1, wherein the presence, absence or level of cortisol, cortisone, 20α-dihydrocortisone, and 20β-dihydrocortisone, 20α-dihydrocortisol, and 20β-dihydrocortisol is determined.

3. The method of claim 1, wherein said sample is an eccrine sweat sample.

4. The method of claim 1, wherein said subject is a human subject.

5. The method of claim 1, wherein said sample is extracted with ethyl acetate prior to said analyzing.

* * * * *